(12) United States Patent
Hoffman et al.

(10) Patent No.: US 8,221,366 B2
(45) Date of Patent: Jul. 17, 2012

(54) VOLUME LIMITING BODILY FLUID DRAINAGE SYSTEM

(75) Inventors: Brian Hoffman, Princeton, NJ (US); Michael McDermott, San Francisco, CA (US); William R. Chang, Colonia, NJ (US); Eric Scott Clasen, Hillsborough, NJ (US)

(73) Assignee: Integra LifeSciences Corporation, Plainsboro, NJ (US)

( * ) Notice: Subject to any disclaimer, the term of this patent is extended or adjusted under 35 U.S.C. 154(b) by 775 days.

(21) Appl. No.: 12/202,809

(22) Filed: Sep. 2, 2008

(65) Prior Publication Data
US 2009/0088710 A1 Apr. 2, 2009

Related U.S. Application Data

(60) Provisional application No. 60/970,236, filed on Sep. 5, 2007.

(51) Int. Cl.
*A61M 1/00* (2006.01)
(52) U.S. Cl. .............. 604/323; 604/27; 604/35; 604/48; 604/65; 604/118; 604/119; 604/317; 604/318; 604/322; 604/326; 137/205; 141/35; 141/59; 141/95; 141/198; 119/14.46
(58) Field of Classification Search .................. 604/322, 604/323, 326
See application file for complete search history.

(56) References Cited

U.S. PATENT DOCUMENTS

| | | | |
|---|---|---|---|
| 1,040,141 A | * | 10/1912 | Canfield ....................... 137/429 |
| 1,527,019 A | * | 2/1925 | Stonier ......................... 137/433 |
| 2,044,816 A | * | 6/1936 | Schmiedeknecht ........... 137/437 |
| 3,989,043 A | | 11/1976 | Dimeff |
| 4,328,820 A | | 5/1982 | Serur |
| 4,500,311 A | | 2/1985 | Redmond et al. |
| 4,681,571 A | * | 7/1987 | Nehring ........................ 604/320 |
| 4,731,056 A | | 3/1988 | Tremulis |
| 4,731,060 A | | 3/1988 | Catalano |
| 4,858,619 A | | 8/1989 | Toth |
| 5,207,661 A | | 5/1993 | Repschlager |
| 5,234,414 A | | 8/1993 | Hung |
| 5,423,346 A | | 6/1995 | Daoud |
| 5,683,357 A | | 11/1997 | Magram |
| 5,683,367 A | | 11/1997 | Jordan et al. |

(Continued)

FOREIGN PATENT DOCUMENTS
EP 1034812 A2 9/2000

*Primary Examiner* — Tatyana Zalukaeva
*Assistant Examiner* — Ilya Treyger
(74) *Attorney, Agent, or Firm* — Thomas A. Runk; Fulwider Patton LLP (57) ABSTRACT

A system and method are disclosed for automatically limiting the drainage of a bodily fluid such as cerebrospinal fluid (CSF) from a patient into a collection chamber. The collection chamber includes a vent having an hydrophobic filter for the passage of air to facilitate the movement of CSF yet to maintain a closed system. The system includes a buoyant float hingedly connected with the top of the collection chamber in one embodiment. When fluid rises in the collection chamber to a predetermined volume, buoyant force raises the float and causes a seal plug mounted on top of the float to seal one of an inflow port or a vent port. The float is limited to pivoting movement in one plane and to a certain angle within that plane. The system and method avoid overdrainage of CSF from the patient and overfilling of the collection chamber.

30 Claims, 7 Drawing Sheets

U.S. PATENT DOCUMENTS

| | | | |
|---|---|---|---|
| 5,730,730 A | 3/1998 | Darling, Jr. | |
| 5,752,281 A * | 5/1998 | Conner | 4/427 |
| 5,772,625 A | 6/1998 | Krueger et al. | |
| 5,885,532 A | 3/1999 | Maltabes et al. | |
| 6,092,547 A * | 7/2000 | Komiya et al. | 137/192 |
| 6,554,806 B2 | 4/2003 | Butterfield et al. | |
| 6,695,004 B1 | 2/2004 | Raybuck | |
| 7,615,036 B2 * | 11/2009 | Joshi et al. | 604/313 |
| 2005/0090775 A1 | 4/2005 | Harper et al. | |
| 2008/0179344 A1 * | 7/2008 | Michaels et al. | 222/20 |

\* cited by examiner

VOLUME LIMITING BODILY FLUID DRAINAGE SYSTEM

BACKGROUND OF THE INVENTION

1. Field of the Invention

The present invention relates generally to medical drainage systems configured to remove bodily fluids from a patient, and more particularly, to a medical drainage system to controllably remove bodily fluids, such as cerebrospinal fluid (CSF), from a patient.

2. Brief Description of Related Art

Cerebrospinal fluid (CSF) is normally a clear watery body fluid that is formed by the human body in the ventricular cavities located within the brain. The CSF flows from the lateral ventricles and third ventricle to the fourth ventricle. Thereafter, the CSF under normal conditions exits the fourth ventricle to flow into the subarachnoid spaces that surround the outside of the brain, the spinal cord, and the lumbosacral nerve roots. The CSF under normal conditions forms at a rate of about 400-500 milliliters per day and is absorbed by the body at the exact same rate, such that the equilibrium between the formation of CSF and the absorption of CSF exists. This balance between the formation of CSF and the absorption of CSF prevents CSF from accumulating under pressure in the central nervous system. A rise in intracranial pressure (ICP) from the accumulation of excess amounts of CSF may lead to headaches, coma, or even death.

Accumulation of CSF above normal physiological levels may occur for a variety of reasons. Blockage of the flow of CSF may cause accumulation of CSF in the ventricles and a rise in ICP. Such blockages to the flow of CSF may result from tumors or may be associated with subarachnoid hemorrhage, for example when an intracranial aneurysm ruptures. Increased intracranial pressures may also occur in pseudotumor cerebri; a condition where more CSF is formed than is absorbed. Furthermore, increased ICP may be associated with infections such as meningitis.

External CSF drainage systems are typically used in a clinical setting when it is desirable to drain CSF through a catheter and into a "closed" collection system to prevent infection of the CSF that may result in meningitis. CSF drainage is desirable in the treatment of patients having increased intracranial pressure (ICP), a condition where the pressure of CSF or brain matter in the skull exceeds the normal upper physiological limits of pressure. External CSF drainage is also desirable to lower increased or normal ICP in patients with pathological CSF leakage from the nose (rhinorrhea) or ears (otorrhea) such as may occur with fractures of the base of the skull. Lowering the ICP frequently allows the fractures to heal and the leak to seal without more aggressive surgical intervention. External CSF drainage is also used in patients with hydrocephalus, a condition where CSF pathologically accumulates in the ventricles of the brain. Furthermore, external CSF drainage is used for temporary drainage when an internalized CSF shunt system fails or is infected.

Some conditions causing increased ICP may be treated by drainage of CSF. Surgical drainage of CSF may be performed by either a ventricular catheter, which is inserted into a lateral ventricle of a cerebral hemisphere, or by a lumbar drainage catheter, which is inserted into the subarachnoid space in the lumbar spine. These catheters allow for removal of excess CSF.

Removal of too much CSF, or "overdrainage," by these catheters is also not desirable. Excessive CSF drainage by ventricular or lumbar catheters may result in severe headaches or collapse of the ventricular cavities. Collapse of the ventricular cavities may cause movement of the cerebral cortex inwardly, sometimes causing traction on veins that rupture and form subdural hematomas. Excessive collapse of the ventricles may also cause shifts of the brain and cerebral arteries, thereby causing re-rupture of an intracranial aneurysm. Measured drainage of the CSF through ventricular or lumbar drainage catheters is highly desirable. Furthermore, drainage of CSF through these catheters is preferably done in a closed system, for example a sealed bag, wherein the CSF has very limited exposure to microbes in room air. CSF is typically sterile when drained from the patient and contamination of the CSF by microbes may have adverse consequences on the patient.

Several drainage systems configured for the generally closed drainage of CSF from either the lumbar subarachnoid space or cerebral ventricles have been described. These drainage systems typically include tubing and one or more valves such as stopcocks to control the flow of CSF from the patient through the drainage catheter. These drainage systems also typically include a sterile bag or other type of container for collection of the CSF.

Clinicians generally wish to limit CSF drainage from the patient to a rate of about 10 milliliters to 50 milliliters per hour so that overdrainage does not occur. Overdrainage of CSF from the patient can result in "overfilling" of the drainage bag which is a condition wherein too much CSF fluid fills the drainage bag. Overfilling a drainage bag or container may cause further problems, including leakage of the fluid from the system and infection through the pathway provided by the leaking fluid.

Overfilling may also cause undesirable CSF contact with portions of a drainage system that function best when kept dry, for example an hydrophobic filter. In certain containers, such as a rigid-wall burette, a vent is required for filling the container and then also for draining the container. To maintain a closed system, a filter is typically located at the vent so that air may leave as the container is being filled and filtered air may enter as the container is being emptied. The vent filter is typically hydrophobic so that liquid within the container does not escape to the environment and liquid outside the container does not enter the container. The filter may also include an anti-microbial substance or it may antimicrobial due to the filter media pore size. Pore size less than three microns is considered to be antimicrobial as bacteria cannot pass through this aperture. CSF typically includes glucose and other proteinaceous substances and should CSF come into contact with a vent filter, it may adhere to the filter thereby making the passage of air through the filter in either direction difficult or impossible. The container would then be rendered useless and must be replaced. Therefore, in the case where a collection container having a vent filter is used for collecting CSF, it would be desirable to limit the amount of CSF flowing into the collection container so that the CSF does not contact the vent filter. Controlling the amount of CSF entering a container has been done in the past by clinicians closely visually monitoring the level of CSF in the container and when the amount reaches a certain level, closing a stopcock to prevent such complications from overdrainage and overfilling. Such monitoring requires the personal attention and time from clinicians who are probably already quite busy.

The flow rate of CSF in many drainage and collection systems is crudely controlled by the level at which the collection system is positioned above the head or spine of the patient being treated. Flow may unexpectedly increase if the level of the system is lowered in relation to the level of the catheter entering the patient. For example, an uncooperative or confused patient may sit up in bed, thereby changing his position farther above where the system has been positioned and result in an increased flow rate of CSF into the drainage and collection system. These systems may further result in overdrainage when the collection container is inadvertently positioned too low and/or drainage goes unnoticed by the busy clinician for some time. A more serious risk can occur when a displaced collection container falls or is compressed thereby forcing a large volume of the collected CSF back into the patient. Flow of CSF through a drain may also suddenly increase with coughing or sneezing by the patient. Excess drainage may also occur from siphoning phenomenon. Overfilling may occur if a busy clinician does not empty the collection chamber of CSF before it fills to undesirable levels. Therefore with these present systems, the amount of CSF flowing out of the patient must be closely monitored by a clinician to prevent complications from overdrainage and overfilling.

Medical drainage systems have been described in the art that include various types of flow or pressure regulating valve systems. The systems sometimes also include a vent system or antisiphoning mechanism. One device known in the art is an external ventricular drainage assembly that includes a ventricular drainage catheter placed in the ventricles of a patient's brain and which is connected to a suture tab for securing the catheter to the patient for preventing relative movement between the catheter and patient. A manually operated valve such as a stopcock is connected to the catheter for selectively opening and closing the external ventricular drainage assembly to fluid flow. An adapter is connected to the stopcock valve for providing access to the fluid flow path within the assembly. A one-way valve such as a miter valve having no moving parts is connected to the adapter. A first length of flexible tubing is connected to the one-way valve and is joined through a connector to a second length of flexible tubing. A collection reservoir is connected to the second length of flexible tubing and includes an entry and outlet port. A drip chamber is positioned between the second length of flexible tubing and the collection reservoir. This is a manually-controlled system as described above.

Another known device is a ventricular drainage system that includes an antisiphon device having a chamber configured for vertical inflow of CSF from the bottom of the chamber to the top of the chamber. An outflow tube is connected at the upper end of the chamber. The device also includes a freely floating ball in the chamber that is capable of closing the inflow tract at the bottom of the chamber when there is no flow of fluid from the ventricular catheter, capable of allowing fluid flow through the chamber during a normal flow of liquid from the catheter and capable of closing the outflow tract upon a rush of fluid from the catheter. Such a system does not account for overfilling.

Also known in the art is a drainage system having an in-line one-way valve for use in the drainage of ventricles of a patient's brain or of the patient's lumbar region and which is connected to a catheter inserted in either the ventricles or lumbar region and secured to the patient. The system includes tubing from the catheter, a four-way stopcock inserted into the tubing followed by a Y-connector providing a sampling site, and a low-pressure one-way valve in line with the tubing to help prevent reflux of fluid into the ventricles or lumbar subarachnoid space. A length of flexible tubing leads from the one-way valve to a burette clamped onto an IV pole, and a drainage bag connected to the bottom of said burette to receive the collected fluid from the burette after it is measured. This system also does not prevent overfilling and requires manual monitoring.

The above devices known in the art all have disadvantages when applied to clinical use for measured CSF drainage. For example, prior art devices do not provide an automatic limitation of flow, or they are complicated and expensive to manufacture, fill from the bottom, clog easily when exposed to proteinaceous fluids, or may hamper the free flow of CSF between a patient and a collection container.

Hence those skilled in the art have recognized a need for a drainage system that avoids conditions of both overdrainage and overfilling. What is needed is a system and method that limit the volume of CSF draining into a collection device such that the volume of drained CSF can be controlled, accurately measured, and configured so that a drainage collection container can be conveniently removed from the bottom of the collection chamber as required. A need also exists for a CSF drainage device that is inexpensive and disposable. There is a further recognized need for a CSF device that provides automatic shut off of fluid flow at a predetermined volume of drainage and which prevents overfilling so as to prevent CSF from coming into contact with a vent filter. The present invention provides solutions to these and other identified needs in the art.

SUMMARY OF THE INVENTION

Briefly and in general terms, the present invention is directed to a system and method for automatically limiting the volume of bodily fluid drained into a collection device. In accordance with aspects of the invention, there is provided a bodily fluid drainage system, comprising a fluid collection chamber formed by a top member connected to a bottom member by a side wall, an inflow port disposed in the top member and configured for receiving bodily fluid into the collection chamber, a vent port disposed in the top member, and a buoyant float member disposed in the collection chamber below the inflow port and pivotably connected with the fluid collection chamber by a hinge such that the float member moves pivotally downward in an open configuration leaving the inflow port open when there is no bodily fluid in the chamber and moves pivotally upward into a closed configuration in response to buoyant force of bodily fluid filling the chamber closing the inflow port when the bodily fluid in the chamber reaches a predetermined level.

In accordance with further aspects, the bodily fluid drainage system further comprises a seal plug mounted on the float member below the inflow port and moving with the float member, located so as to allow flow of bodily fluid through the inflow port into the collection chamber in the open configuration when the chamber has no fluid in it and closes the inflow port so as to prevent the flow of bodily fluid through the inflow port into the collection chamber in the closed configuration when a predetermined volume of bodily fluid collects in the collection chamber.

In a more detailed aspect, the seal plug has a conical shape, a diameter of which is larger than an opening of the inflow port to completely block the inflow port when in the closed configuration to prevent the flow of bodily fluid into the chamber. The conical shape of the seal plug includes an apex, the float member and seal plug disposed in the chamber so that the apex is within the inflow port when in the open configuration and also when in the closed configuration.

Further aspects in accordance with the invention comprise the float member including a top portion at which is disposed a hollow chimney extension having a pressure equalization hole at a top surface, the pressure equalization hole configured to communicate with an interior of the float member to equalize interior pressure with outside pressure wherein a length of the hollow chimney extension is selected to place the equalization hole high up in the collection chamber above the collected fluid level thereby preventing the collected fluid from entering the float member lumen under normal operating conditions. The pressure equalization hole has a diameter that is selected to be small in size so that it inhibits the movement of the bodily fluid through the equalization hole to thereby avoid changes in buoyancy of the float member.

Additional more detailed aspects include a seal plug mounted on a top portion of the float member below the inflow port and moving with the float member, and located so as to allow flow of bodily fluid through the inflow port into the collection chamber in the open configuration when the chamber has no fluid in it and closes the inflow port so as to prevent the flow of bodily fluid through the inflow port into the collection chamber in the closed configuration when a predetermined volume of bodily fluid collects in the collection chamber, wherein the seal plug is positioned on the float member between the chimney extension and the hinge. In another aspect, the seal plug is positioned adjacent the hinge.

In yet more detailed aspects, the hinge includes a hinge arm having a width disposed on the float member two hinge pins located on either side of the hinge arm, wherein the width of the hinge arm and locations of the pins are selected to provide torsional stability to the float member, and two hinge pin receiving members disposed on the fluid collection chamber for receiving the two hinge pins to thereby pivotally mount the float member. In a more detailed aspect, the hinge pin receiving members are located on the top member. In another aspect, the float member is configured so that its pivotal movement is limited to a predetermined angle. In more detailed aspects regarding the float configuration, the side wall has an inner surface having an inner diameter, and the float member has a bottom portion having an outer diameter that is smaller than the inner diameter of the side wall by a predetermined distance such that pivotal movement of the hinged float member in the direction of the open configuration is limited to the predetermined angle by contact of the bottom portion of the float member with the inner surface of the side wall.

Yet further detailed aspects include a filter connected to the vent port. The filter in one aspect is configured to be hydrophobic. The filter in another aspect is configured to be anti-microbial. The side wall of the fluid collection chamber is transparent so that contents of the collection chamber can be seen directly through the side wall. The side wall of the fluid collection chamber includes volume markings. The top member in another aspect also includes a vent chamber in connection with the vent port and within which is disposed a vent filter. In certain aspects, the vent filter may be hydrophobic and/or microbial.

In accordance with a volume-limited cerebrospinal fluid (CSF) drainage system, there is provided a CSF collection chamber formed by a top member connected to a bottom member by a side wall, an inflow port disposed in the top member and configured for receiving CSF into the collection chamber, a vent port disposed in the top member, a vent chamber including an hydrophobic filter connected with the vent port, a buoyant float member having a top portion and a bottom portion disposed in the collection chamber below the inflow port, the float top portion being pivotably connected with the top member of the chamber by a hinge such that the float member moves pivotally downward to an open configuration leaving the inflow port open when there is no CSF in the chamber and moves pivotally upward to a closed configuration in response to buoyant force of CSF flowing into the chamber closing the inflow port when the CSF in the chamber reaches a predetermined level, and a seal plug mounted on the top portion of the float member below the inflow port and moving with the float member so as to allow flow of CSF through the inflow port into the collection chamber in the open configuration and moving with the float member so as to prevent the flow of CSF through the inflow port into the collection chamber in the closed configuration when a predetermined volume of CSF collects in the collection chamber, wherein the seal plug has a conical shape, a diameter of which is larger than an opening of the inflow port to completely block the inflow port when in the closed configuration to prevent the flow of CSF into the chamber, the top portion of the float member includes a hollow chimney extension having a pressure equalization hole at a top surface, the pressure equalization hole configured to communicate with an interior of the float member to equalize interior pressure with outside pressure, wherein a length of the hollow chimney extension is selected to place the equalization hole high up in the collection chamber above the collected CSF level thereby preventing the collected CSF from entering the float member lumen under normal operating conditions, wherein the pressure equalization hole has a diameter that is selected to be small in size so that it inhibits the movement of CSF through the equalization hole to thereby avoid changes in buoyancy of the float member, wherein the seal plug is positioned on the float member between the chimney extension and the hinge and adjacent the hinge; and wherein the wall of the fluid collection chamber is transparent so that contents of the collection chamber can be seen directly through the wall.

In accordance with aspects of a method in accordance with the invention, there is provided a method of controlling the flow of bodily fluid comprising the steps of receiving the bodily fluid in a collection chamber through an inflow port disposed in a top of the chamber, accumulating the received bodily fluid in the chamber to form a fluid surface in the chamber that rises as the bodily fluid is accumulated and that develops a buoyant force, applying the buoyant force to a float member disposed within the collection chamber that is hingedly mounted, moving the float member upwards in a pivoting motion about the mounting hinge toward the top of the chamber as a result of the buoyant force, and blocking the inflow of further bodily fluid with the float member upon accumulating a predetermined volume of bodily fluid in the chamber.

In further detailed aspects, the method further comprises the step of venting the collection chamber through a vent port so that air within the chamber is vented to outside atmosphere during the step of accumulating the received bodily fluid. The step of venting further comprises preventing the passage of liquid during the venting step. The step of venting also includes forcing vented air into contact with an anti-microbial agent. The step of blocking the inflow comprises sealing the inflow port or vent port with a seal plug mounted to the float member. In another detailed aspect, the seal plug has an apex disposed so that it is always within the inflow port whether the collection chamber is empty or is full.

The method further comprises the step of limiting torsional movement of the float member so that movement of the float member is substantially confined to pivoting movement in one plane. The method further comprises limiting pivotal movement of the float member to a predetermined angle.

In another aspect in accordance with the invention, there is provided a bodily fluid drainage system, comprising a fluid collection chamber formed by a top member connected to a bottom member by a side wall, an inflow port disposed in the top member and configured for receiving bodily fluid into the collection chamber, a first vent port disposed in the top member, and a buoyant float member disposed in the collection chamber below the top member and pivotably connected with the fluid connection chamber by a hinge such that the float member moves pivotally downward in an open configuration leaving at least one of the inflow port or the first vent port open and moves pivotally upward in a closed configuration in response to buoyant force of bodily fluid filling the chamber closing at least one of the inflow port or the vent port when the bodily fluid in the chamber reaches a predetermined level. In another feature, the bodily fluid drainage system further comprises a second vent port disposed in the top member configured to permit air to flow into the collection chamber.

In accordance with more detailed aspects, the bodily fluid drainage system further comprises a one-way valve mounted in the second vent port to permit air to flow into the collection chamber through the second vent port but to prevent air from flowing out of the chamber through the second vent port and wherein the buoyant float member is further configured to move pivotally downward in an open configuration leaving the first vent port open and to move pivotally upward in a closed configuration in response to buoyant force of bodily fluid flowing into the chamber closing the first vent port when the bodily fluid in the chamber reaches a predetermined level. The bodily fluid drainage system further comprises an outlet port located at the bottom member through which fluid may flow out of the collection chamber wherein the one-way valve has a cracking pressure that is selected to be approximately equal to a pressure differential created within the collection chamber by fluid flowing out through the outlet port.

In more detailed aspects, the inlet port is located in the top member at a position opposite the hinge position and wherein the collection chamber has an inner diameter and the buoyant float member has an outer diameter that is selected to be smaller than the inner diameter such that the buoyant member is not located under the inlet port in either the open or closed configurations. Furthermore, the side wall of the fluid collection chamber is transparent so that the flow of bodily fluid into the collection chamber through the inflow port can be seen directly through the side wall.

In other more detailed aspects, the bodily fluid drainage system comprises a seal plug mounted on the float member below the first vent port and moving with the float member, the seal plug being located so as to allow air to flow out of the first vent port from the collection chamber in the open configuration when the chamber has no fluid in it and closes the first vent port so as to prevent the flow of air out of the collection chamber in the closed configuration when a predetermined volume of bodily fluid collects in the collection chamber.

In a more detailed aspect, the seal plug has a conical shape, the diameter of which is larger than an opening of the first vent port to completely block the first vent port when in the closed configuration to prevent the flow of air out of the chamber. The conical shape of the seal plug includes an apex, the float member and seal plug disposed in the chamber so that the apex is within the first vent port when in the open configuration and also when in the closed configuration.

In yet other aspects, the float member includes a top portion at which is disposed a hollow chimney extension having a pressure equalization hole at a top surface, the pressure equalization hole configured to communicate with an interior of the float member to equalize interior pressure with outside pressure wherein a length of the hollow chimney extension is selected to place the equalization hole high up in the collection chamber above the collected fluid level thereby preventing the collected fluid from entering the float member lumen under normal operating conditions. The bodily fluid drainage system wherein the hinge includes a hinge arm having a width disposed on the float member, two hinge pins located on either side of the hinge arm, wherein the width of the hinge arm and locations of the pins are selected to provide torsional stability to the float member, and two hinge pin receiving members disposed on the collection chamber for receiving the two hinge pins to thereby pivotally mount the float member to the top member. In a more detailed aspect, the hinge pin receiving members are mounted to the top member.

In yet further more detailed aspects, the float member is configured so that its pivotal movement is limited to a predetermined angle. The side wall has an inner surface having an inner diameter, and the float member has a bottom portion having an outer diameter that is smaller than the inner diameter of the side wall by a predetermined distance such that pivotal movement of the hinged float member in the direction of the open configuration is limited to the predetermined angle by contact of the bottom portion of the float member with the inner surface of the side wall.

The features and advantages of the invention will be more readily understood from the following detailed description which should be read in conjunction with the accompanying drawings.

DETAILED DESCRIPTION OF THE PREFERRED EMBODIMENTS

Referring now in more detail to the exemplary drawings for purposes of illustrating embodiments of the invention, wherein like reference numerals designate corresponding or like elements among the several views, an embodiment of a body fluid drainage system for volume limited drainage of a body fluid, such as cerebrospinal fluid (CSF), is illustrated in FIGS. 1-8 in accordance with aspects of the present invention.

Figure 1:
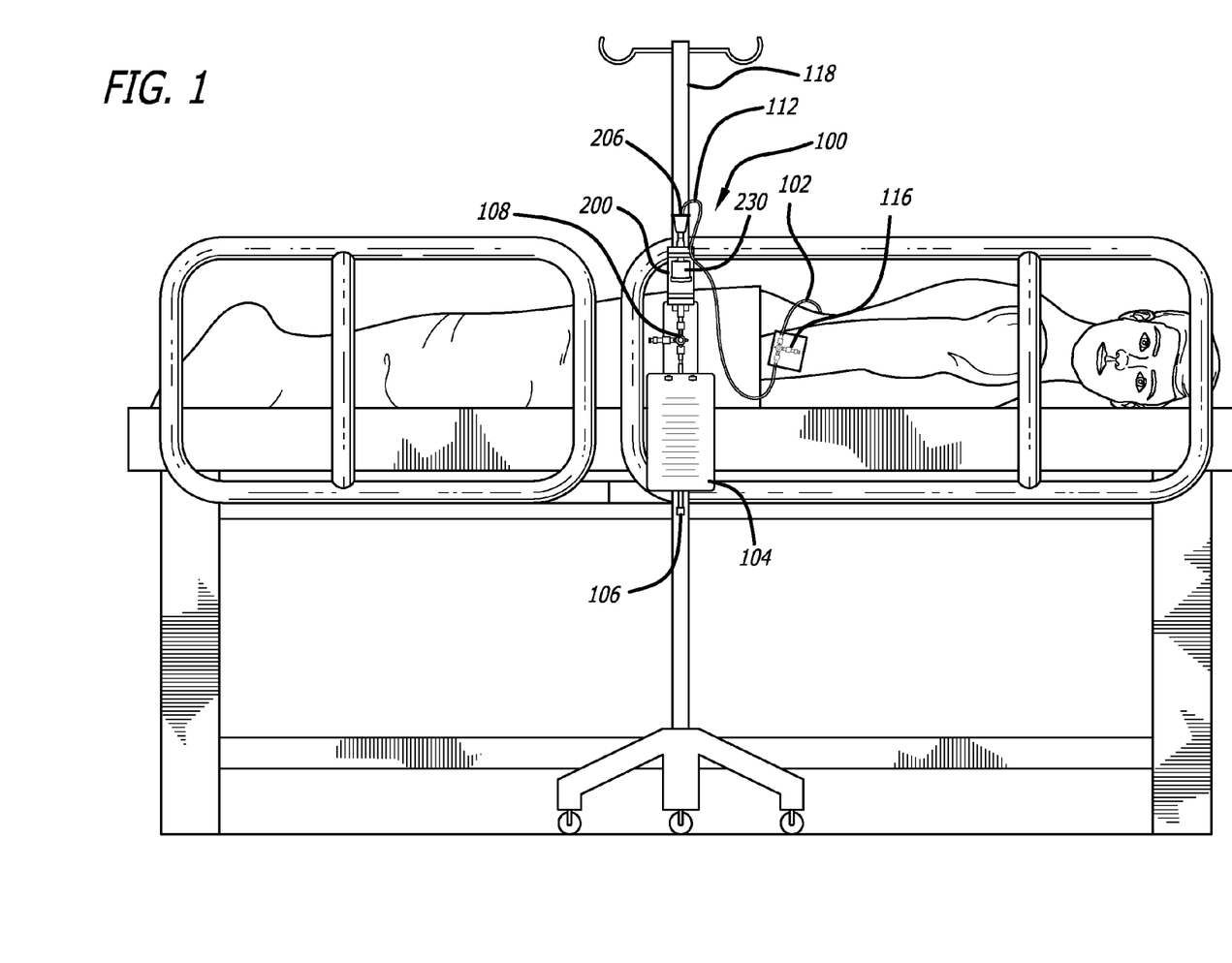
FIG. 1 illustrates one embodiment of a volume limiting cerebrospinal fluid drainage system wherein the system includes a lumbar drainage catheter positioned in a patient to be treated, a bodily fluid collection chamber, and a drainage bag with control valves or stopcocks position along the fluid passage for manual control over drainage.

Referring first to FIG. 1, one embodiment of the fluid drainage system 100 of the present invention is adapted to drain cerebro-spinal fluid (CSF) from the lumbar subarachnoid space of a patient. The drainage system includes a catheter 102 adapted to be inserted into the lumbar subarachnoid space through the low back of a patient to be treated. In another embodiment, the catheter may be inserted into the lateral ventricles of the patient to be treated to drain CSF from the brain. In yet another embodiment, bodily fluids from other anatomical locations or body cavities in a patient may be drained using the system. In one embodiment, for example, accumulated fluid may be drained through the catheter from the peritoneal cavity of a patient with ascites. The drainage system further includes a flow limiting collection chamber 200, and a drainage bag 104 having a drainage port 106. The collection chamber and drainage bag are preferably vertically mounted on a pole 118, for example an IV pole, positioned adjacent the patient to be treated. Alternatively, the collection chamber and drainage bag may be vertically mounted on the patient's hospital bed. The pressure at which CSF flows into the collection chamber is determined by the height of the system in relation to the patient. The rate of flow of CSF is controlled by the volume of CSF flowing into the collection chamber and the timing of the clinician periodically emptying the collection chamber. The rate of flow of CSF is determined by the volume of CSF flowing into the chamber over time, and the time periods between manual emptying of the collection chamber by the clinician.

Figure 2:
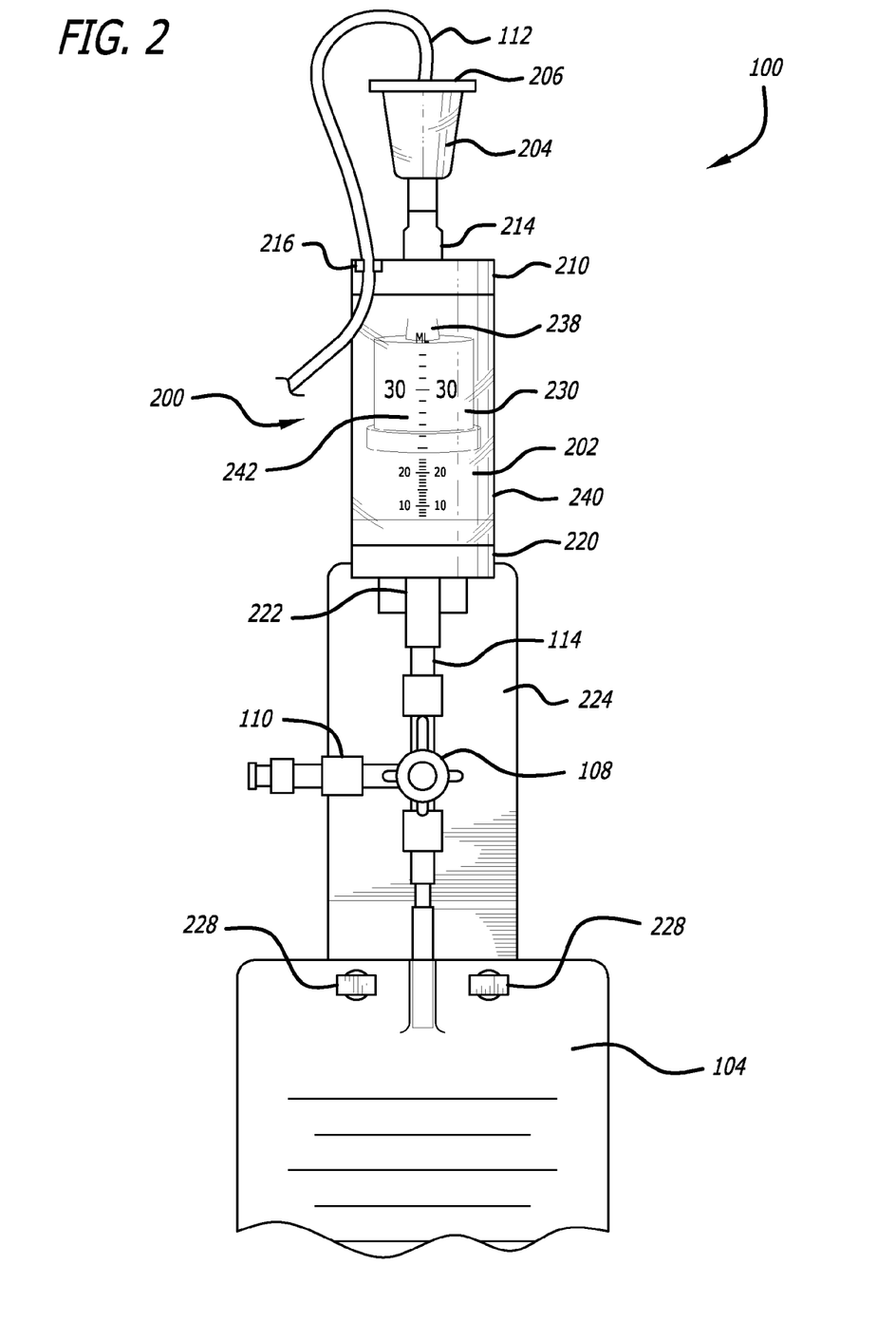
FIG. 2 is a frontal plan view of a portion of the volume limiting cerebrospinal fluid drainage system of FIG. 1 showing a vented bodily fluid collection chamber and the top of a drainage bag with a stopcock position between the two to manually control the flow of fluid.
Figure 3:
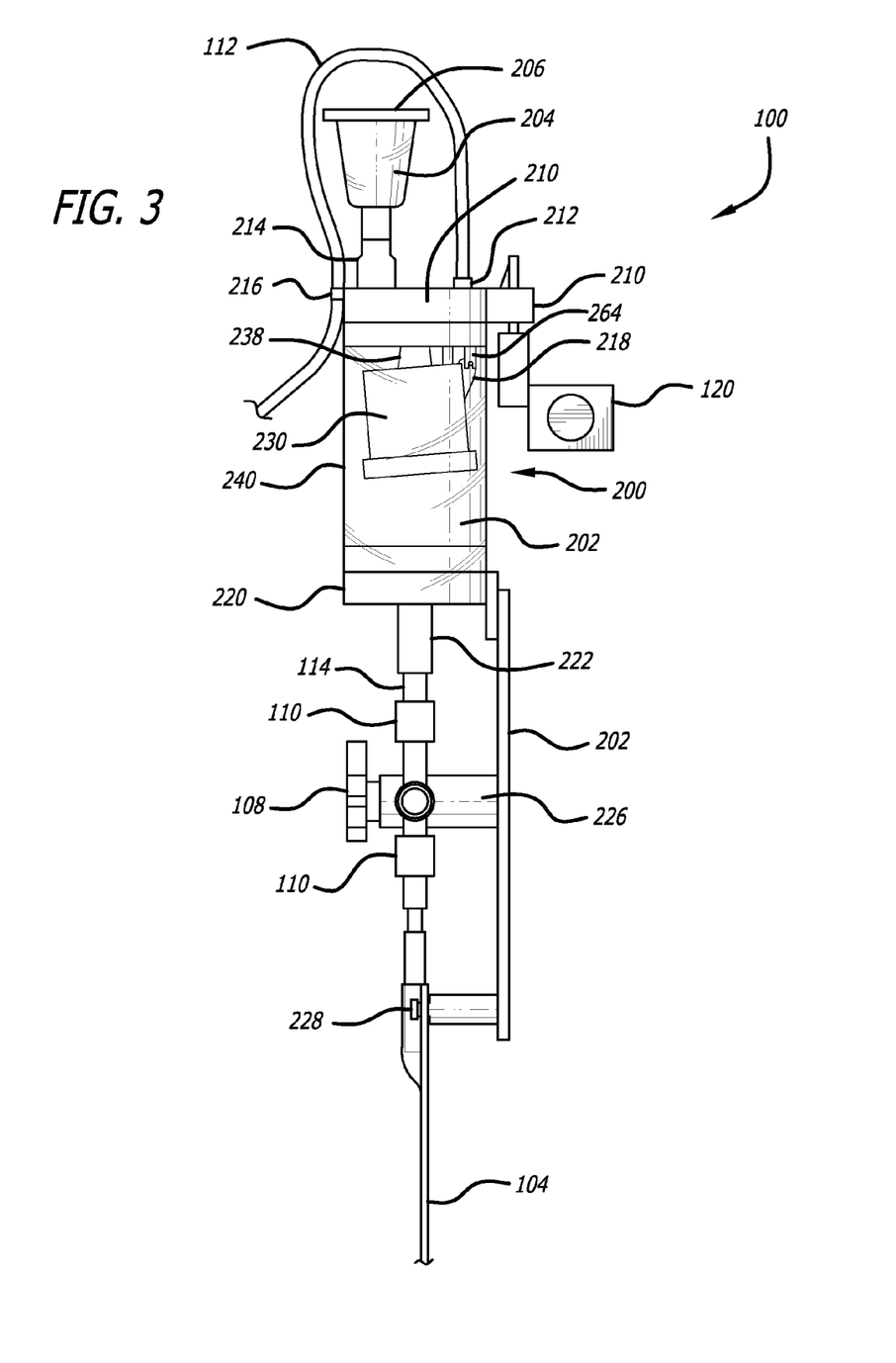
FIG. 3 is a right-side plan view of the portion of the volume limiting cerebrospinal fluid drainage system of FIG. 2.
Figures 4, 5:
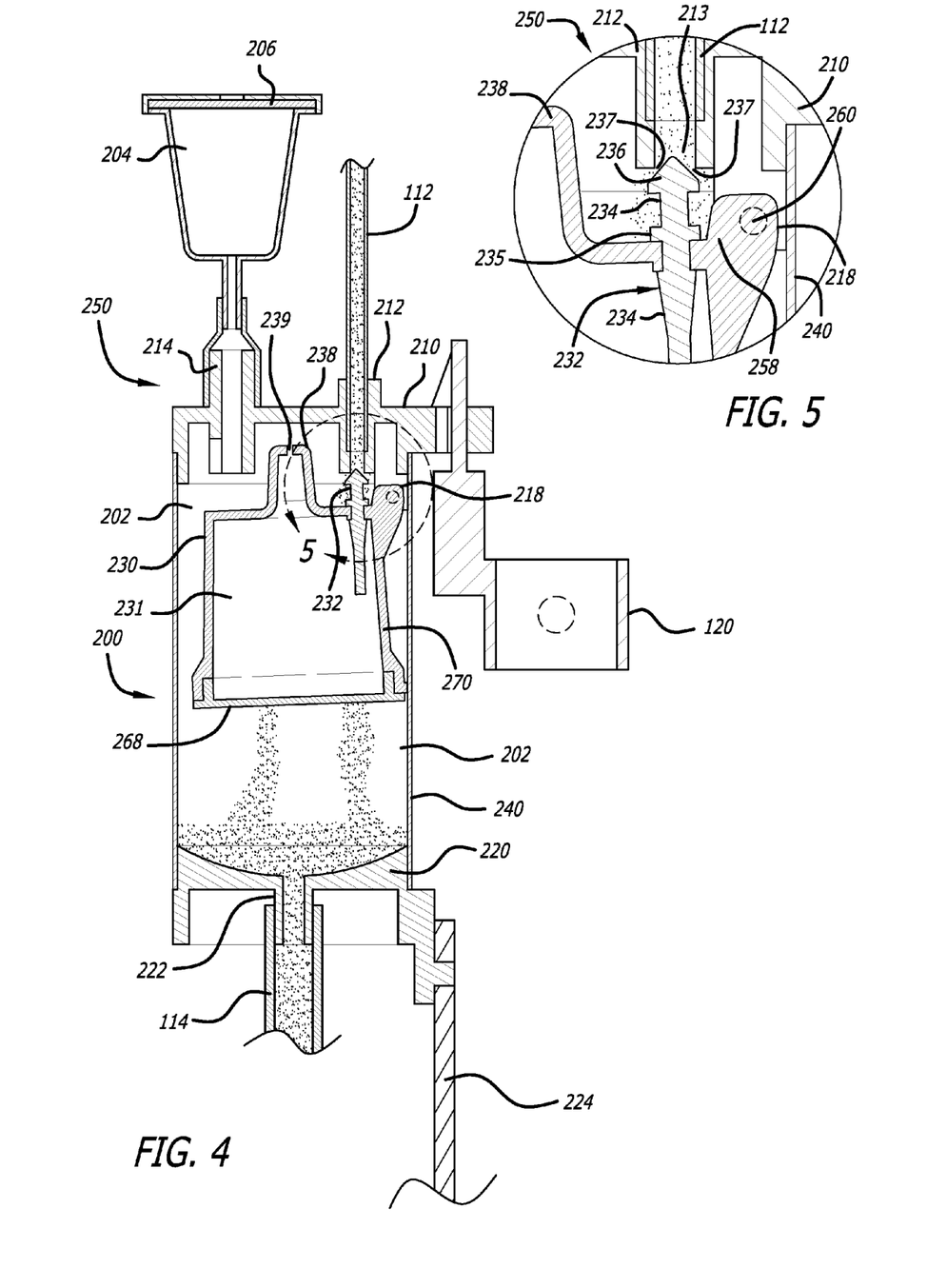
FIG. 4 is a right-side cross-sectional view of the vented bodily fluid collection chamber of FIG. 3 showing an internal float member in an open configuration.
FIG. 5 is a magnified cross-sectional view through a portion of the volume limiting cerebrospinal fluid drainage system shown in FIG. 4 in which details of a hinge and a seal plug located within the inflow port during the time the float member is in the open configuration are more clearly shown.

Referring also now to FIGS. 2-4, the collection chamber 200 has a lumen 202 and is formed from a top member 210 connected with a bottom member 220 by a wall 240. The wall may have indicia and/or markings 242 configured for indicating the volume of CSF contained within the collection chamber. In one preferred embodiment, the wall is cylindrical and transparent so that the clinician may view the contents of the chamber and thereby accurately measure the amount of drained CSF in the collection chamber. The volume of drained CSF in the collection chamber 200 may be seen and measured by the clinician using the volume markings 242 on the transparent wall 240 of the collection chamber. In one embodiment, the volume markings may be spaced apart such that each volume marking represents 10% of the total volume of the collection chamber lumen 202. In another embodiment, the volume markings may be spaced apart such that each volume marking represents 1 milliliter. A larger font may be used for the volume markings at each 10 milliliters of volume. The volume markings may be spaced further apart on the collection chamber wall at volume levels where the collected fluid may contact the float member 230, because the float member occupies some of the volume within the collection chamber at such levels. Volume markings may also be disposed on the drainage bag 104 (FIG. 1). The drainage bag may be provided in a variety of sizes. In one embodiment the drainage bag is configured to hold a volume of 1000 milliliters and is detachably connected to the outflow tubing 114 so that such drainage bags can easily be replaced when filled with drained fluid.

An inflow port 212 having a lumen is disposed in the top member. A vent port 214 having a lumen is also included in the top member. The vent port is connected with a vent chamber 204 that includes a filter 206. In one embodiment, the filter is preferably hydrophobic and antimicrobial. As used herein, "hydrophobic" is used to mean repelling water or preventing the passage of liquid. "Antimicrobial" is used to mean destructive to, or preventing the development of, or passage of, microorganisms, or an agent that destroys or prevents the development of microorganisms. However, the filter may simply be hydrophobic without being antimicrobial in another embodiment.

The system is configured so that the volume of the vent chamber is approximately 2 milliliters to 15 milliliters. This reduced volume, and the hydrophobic filter provide an effective seal to CSF leakage, and prevent drainage even if the system falls to the floor or the volume limiting features described in more detail below are not capable of functioning. An outflow port 222 having a lumen and configured for draining CSF out of the collection chamber is disposed in the bottom member. An inflow tubing 112 having a lumen is disposed between the catheter 102 (FIG. 1) and the inflow port 212 for permitting the flow of CSF into the collection chamber. An outflow tubing 114 having a lumen is disposed between the outflow port 222 and the drainage bag 104. The system 100 is thereby configured with a potential fluid flow path for CSF from the patient to the drainage bag through the catheter, inflow tubing, inflow port, collection chamber lumen, outflow port, and outflow tubing.

A valve 108 known in the art, such as a stopcock or a clamp, may be disposed in the system to manually regulate the drainage of CSF, or to provide an access site for sampling the CSF for laboratory examination. Preferably, at least one valve 108 is positioned between the outflow tubing 114 and the drainage bag 104 to allow for manual regulation of the flow of CSF from the collection chamber 200 to the drainage bag. The valve disposed between the collection chamber 200 and the drainage bag may be manually opened to drain CSF into the drainage bag, for example, after the clinician measures the volume of CSF in the collection chamber. In at least one other embodiment, the outflow port 222 may, however, be directly connected with the drainage bag by at least one stopcock, thereby eliminating the need for the outflow tubing 114. Referring briefly again to FIG. 1, at least one stopcock 110, or other type of valve, may be positioned between the catheter 102 and inflow tubing 112, for example to obtain samples of CSF from the patient, to shut off flow to the collection chamber while the patient is transported, or if the clinician wishes to exchange the collection chamber for a new one.

Figures 6, 7:
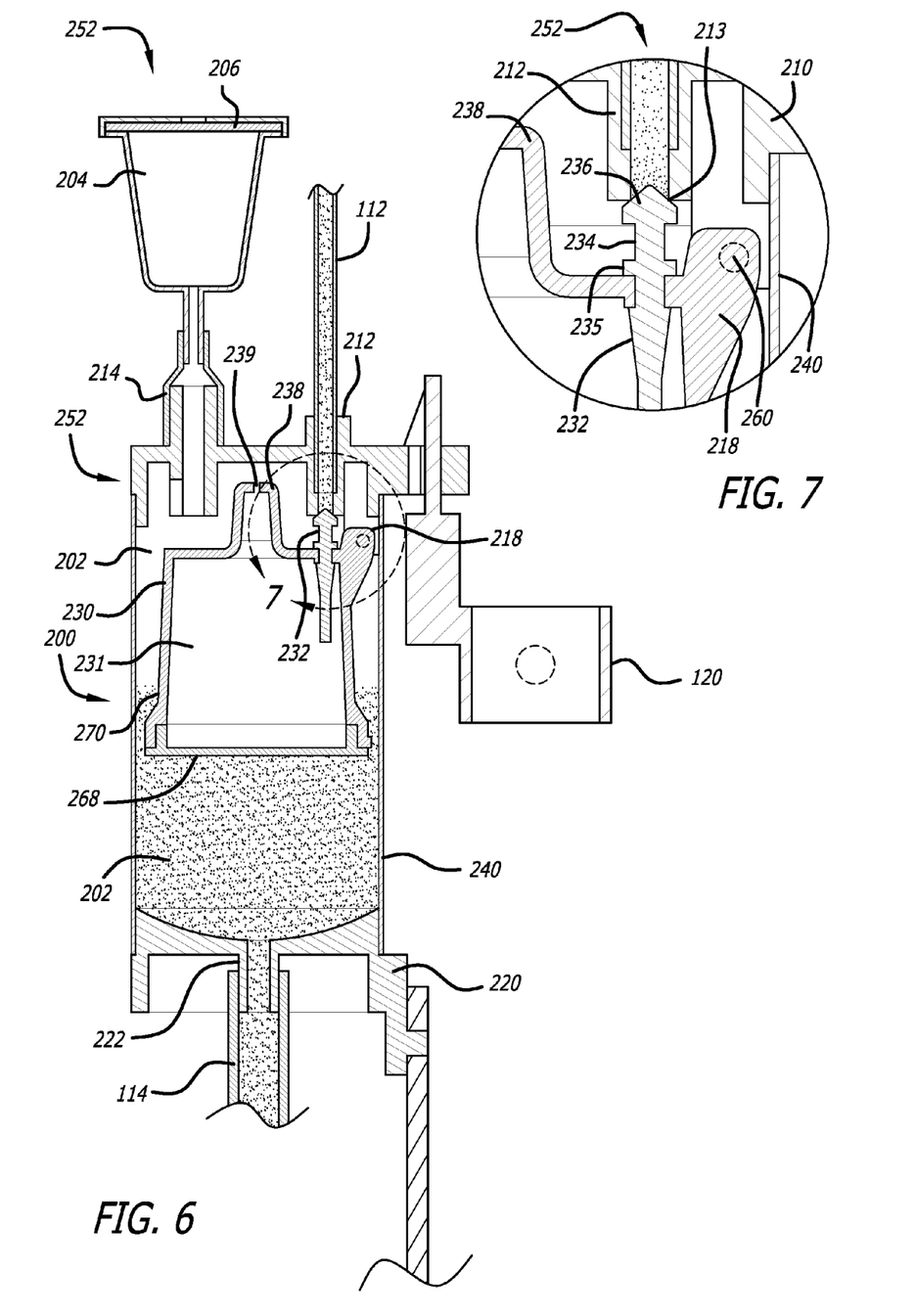
FIG. 6 is right-side cross-sectional view of a portion of the vented bodily fluid collection chamber of FIG. 3 wherein the float member located within the chamber is shown in the closed configuration with buoyant force of the bodily fluid forcing the float member upward.
FIG. 7 is a magnified cross-sectional view through a portion of the volume limiting cerebrospinal fluid drainage system shown in FIG. 6 in which the seal plug is shown located between a chimney extension of the float member and the hinge, and is within the inflow port to close the inflow port against further fluid draining into the collection chamber.

Referring again now to FIGS. 2-4, and also to FIGS. 5-7, the collection chamber 200 further includes a buoyant float member 230 that is pivotably connected with the top member 210 by a hinge 218. In at least one embodiment, a float member lumen 231 is filled with air. In other embodiments, the float member lumen may be filled with other gases, or buoyant materials known in the art. A seal plug 232 is disposed on the top of the float member adjacent the hinge. The seal plug includes a plug head 236 and a plug support 234. In one embodiment, the plug head is conical in configuration and the plug support is substantially cylindrical, further including a fitting 235 for attaching the seal plug to a hole in the float member. The seal plug head is configured to allow flow into the chamber in an open configuration 250 and to seal an opening 213 in the inflow port 212 in a closed configuration 252. Flow of CSF from the patient to the collection chamber through the inflow port to fill the chamber is thereby prevented in the closed configuration. The seal plug is further configured to disengage from the inflow port opening and return to the open configuration when fluid in the collection chamber is drained into the drainage bag 104. The seal plug and hinge are discussed in more detail below.

In one preferred embodiment, the float member 230 includes a hollow chimney extension 238 having a pressure equalization hole 239 at the top. The pressure equalization hole communicates with air inside the float member lumen 231. The pressure equalization hole permits gases under pressure to flow into or out of the float member lumen 231 through the pressure equalization hole. The pressure equalization hole prevents pressure differences from developing between the inside and outside of the float member during the sterilization process, thereby preventing damage to the float member during sterilization under pressure. The hollow chimney extension is advantageously configured to place the equalization hole high up in the collection chamber 200 and well above the collected fluid level, thereby preventing CSF from entering the float member lumen. The diameter of the equalization hole may be minimized to a size that allows movement of gases but inhibits movement of fluid through the equalization hole. Fluid in the float chamber lumen is preferably avoided because such fluid may affect buoyancy. In one embodiment, the float member is formed by connecting a float member chamber 270 with a float member bottom cap 268.

The present invention provides added patient safety by stopping flow at a prescribed volume. Clinicians generally wish to drain patient CSF in quantities between 10 milliliters and 50 milliliters per hour. At least one embodiment includes a collection chamber 200 that provides for a prescribed fluid drainage limit of 20 milliliters of fluid. At least one other embodiment includes a collection chamber 200 that provides for a prescribed fluid drainage limit of 30 milliliters of fluid. Still other embodiments may limit drainage of fluid to volumes ranging from 10 milliliters to a larger quantity, such as 200 milliliters. In at least one embodiment, the float member 230 occupies a volume of about 10 milliliters to about 15 milliliters. The collection chamber lumen 202 is therefore preferably configured with a volume about equal to, or slightly larger than the float member volume plus the prescribed volume. In one embodiment, the volume of the collection chamber exceeds the combined volumes of the float member and the prescribed volume by about two milliliters to about ten milliliters.

When the collection chamber 200 is void of fluid, the float member 230 is configured to be in an open configuration 250 (FIGS. 4 and 5) that permits flow of CSF through the inflow port 212 into the collection chamber. In the open configuration, there is a gap 237 (FIG. 5) between the seal plug head 236 and the inflow port, such that CSF can flow through the inflow port opening 213 and into the collection chamber. When the fluid in the collection chamber reaches the prescribed volume, the buoyant float member is configured to lift towards the top member 210 and pivot at the hinge 218 to a closed configuration 252 (FIGS. 6 and 7). Referring specifically now to FIG. 7, in the closed configuration, the plug head 236 has advanced into the inflow port opening, obliterating the gap and sealing the inflow port 212, thereby substantially stopping the flow of CSF from the patient to the collection chamber through the inflow port.

In at least one embodiment, the gap 237 between the seal plug head 236 and the inflow port 212 opening 213 may be configured such that the float member must pivot at the hinge 218 only a minimal amount from the open configuration (FIGS. 4 and 5) to the closed configuration (FIGS. 6 and 7) to close the gap and stop the flow of CSF between the patient and the collection chamber 200. A small gap is preferred to keep the seal plug head aligned with the inflow port opening at all times. In at least one preferred embodiment, the seal plug head has a conical shape, such that the apex of the tip of the seal plug head is positioned slightly within the inflow port opening in the open configuration (FIG. 5). The seal plug head therefore needs to advance into the inflow port opening only a small distance before the gap is closed and the seal plug head seals flow through the inflow port opening. The seal plug head may, however, be other shapes, for example spherical or oblong. In one embodiment, the gap is closed when the hinge pivots less than five degrees from the open configuration. In another embodiment, the gap is closed when the hinge pivots less than ten degrees from the open configuration. In still another embodiment, for example, the gap is closed when the hinge pivots less than twenty degrees. The seal plug head is preferably formed from a pliable yet resilient material such as silicone. The seal plug is configured such that it releasably mates with the inflow port to stop flow through the inflow port opening. The seal plug head is configured to dislodge from the inflow port opening when fluid is drained out of the collection chamber from the outflow port 222, wherein the system is returned to the open configuration 250, and further flow into the collection chamber is permitted. The seal plug is elastically compliant to accommodate an accumulation of tolerances between the float member and the inflow port that could produce a misalignment between the seal plug and inflow port sufficient to prevent said seal plug from fully closing the inflow port when the bodily fluid has reached the predetermined level.

The seal plug 232 shown in FIGS. 4 through 9 has a conical head 236. As such, it is tapered along its length and therefore has multiple varying diameters. Some of those diameters, such as at the apex, will fit within the port with which the head 236 is paired and at least one section of the head will have a diameter that is larger than the opening of the port with which it is paired. Also, the seal plug may take forms differing from the conical shape shown in the accompanying figures. As one example, the seal plug may fit over the outside of the port as opposed to fitting within the inside. Other configurations for a seal plug are possible.

Figure 8:
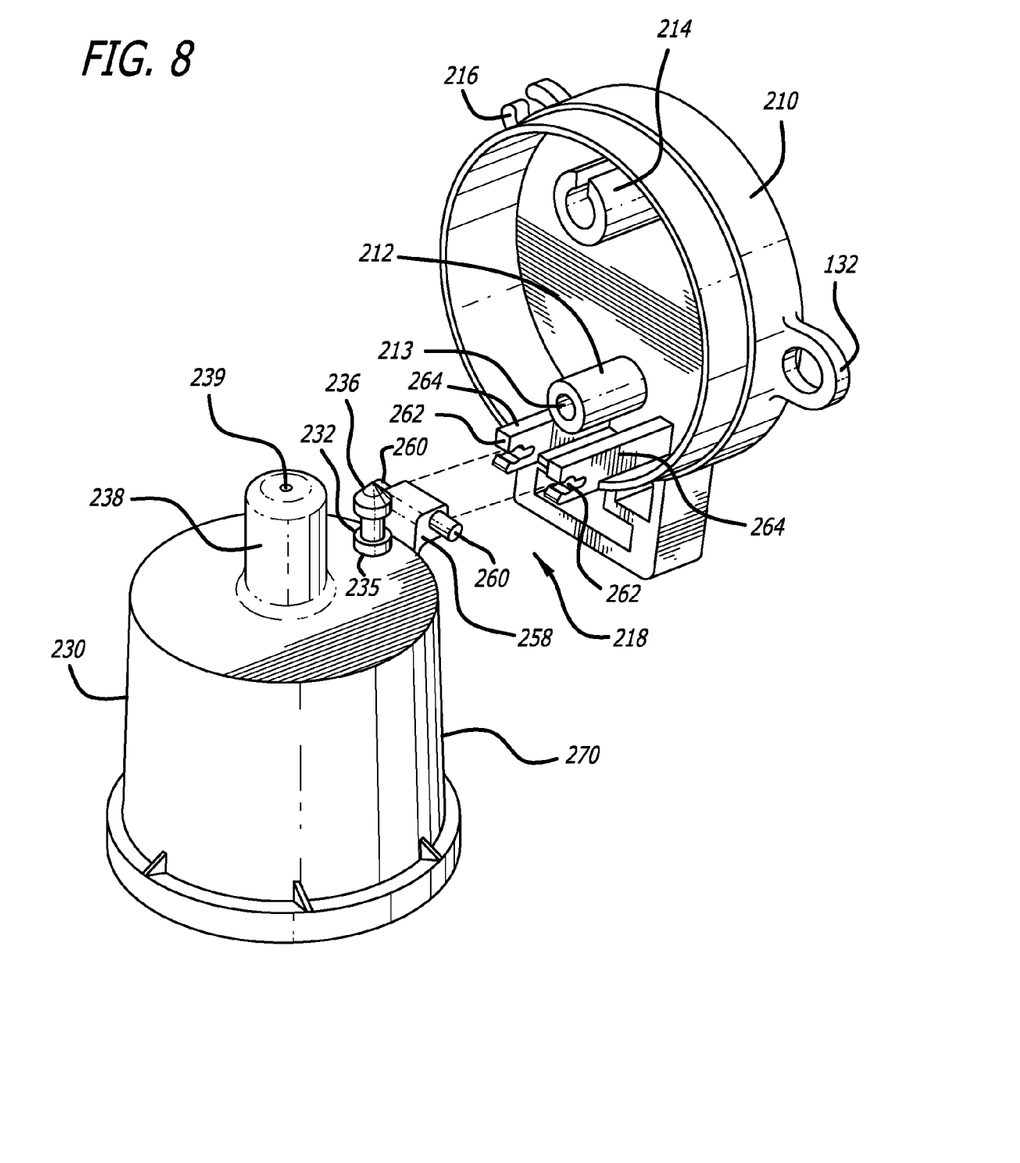
FIG. 8 is an exploded perspective view of the float member and a top member of the fluid collection chamber of the volume limiting cerebrospinal fluid drainage system of FIG. 1 showing more details of the hinge used to provide increased torsional stability to the float member.

Referring also now to FIG. 8, in at least one embodiment, a hinge 218 includes a hinge arm 258 connected with the float member 230. In at least one embodiment, the hinge arm is connected with the float member generally adjacent the seal plug 232. Placement of the seal plug close to the hinge is advantageous in keeping the head 236 of the seal plug reliably aligned with the inflow port 212 opening 213. Placement of the seal plug close to the hinge is also advantageous in maximizing leverage forces of the seal plug into the inflow port opening. In one embodiment shown in FIG. 8, the forces applied by the seal plug against the inflow port are about three times the buoyancy forces applied upon the float member by the prescribed volume of collected fluid.

In one preferred embodiment, the hinge 218 has a snap fit configuration. Two hinge pins 260, having longitudinal axes coaxially aligned with each other and with the center of rotation of the hinge, are disposed at a distance from each other on the hinge arm 258. The hinge further includes two hinge pin receiving members 262, which are disposed on the top member 210 of the collection chamber 200. The hinge pin receiving members are configured to receive the hinge pins to form the pivotable hinge. The hinge pin receiving members may be connected with the top member by hinge pin receiving member supports 264. When the hinge pins are connected with the hinge pin receiving members to form the hinge, the separation of the two hinge pins on the hinge arm is advantageous in preventing torsional forces from misaligning the seal plug and the inflow port 212 opening 213 during movement between the open configuration 250 (FIGS. 4 and 5) and the closed configuration 252 (FIGS. 6 and 7). The fit of the hinge pins into the hinge pin receiving members is configured to minimize friction between the hinge pins and the hinge pin receiving members, thereby allowing relatively free pivotable motion at the hinge. A snap fit hinge is advantageous in minimizing the costs of manufacturing the system 100. Slots configured in the pin receiving members may be provided to aid in snapping the hinge pins into the receiving members.

Drainage rate into the collection chamber 200 is a function of time and the height difference between the patient and the collection system, for example the top member 210 of the fluid collection chamber. The rate, volume, and pressures at which CSF flows from the patient to an empty collection chamber are determined by the clinician. The collection chamber may be aligned in relationship to bodily landmarks such as the Foramen of Monro or the shoulder, or to the point of entry of the drainage catheter into the patient. The present invention is advantageous because the volume of CSF flowing from the patient to the collection chamber 200 at the set position is automatically controlled and limited. Complications resulting from overdrainage and/or overfilling of CSF are at least reduced or are completely avoided. Furthermore, the present invention frees the clinician from constant monitoring of the amount of CSF drainage coming out of a patient while accurately measuring the volume of CSF flow. The device 200 adds safety to the procedure of CSF drainage by preventing overdrainage and/or overfilling from a poorly positioned collection chamber. When properly used in an upright position, the device may further prevent retrograde flow from the collection chamber to the patient, thereby reducing the risk of CSF infection in the patient.

Referring again to FIGS. 4 and 6, the system 100 includes a second safety feature that prevents overdrainage and/or CSF leakage from the system. That feature is an hydrophobic filter 206 that is included in a vent chamber 204 that is connected with a vent port 214 disposed on the top member of the fluid collection chamber. The hydrophobic filter is advantageous in preventing contamination of sterile internal portions of the system by microbes, and preventing leakage of CSF out of the system. The system is configured so that the volume of the vent chamber is small, for example, only approximately 2 milliliters to 15 milliliters. This reduced volume, and the hydrophobic filter provide an effective seal to CSF leakage, and prevent drainage of the CSF out of the chamber 200 even if the system falls to the floor in a configuration where the float member 230 is not capable of functioning to stop flow of CSF from the patient. Such failure of the automatic shut off of CSF flow by the float member 230 may occur due to stress, tilt, or damage. In at least one embodiment, this system configuration provides an effective seal to CSF leakage even in the event that the seal plug 232 fails to seal the inflow port opening 213. The filter prevent the escape of CSF and the volume of the vent chamber will accept no more than eighteen milliliters over the prescribed volume of the collection chamber at a pressure of 122 centimeters of $H_2O$. As mentioned previously, the filter 206 may also include an antimicrobial agent.

Repeated contact of an antimicrobial filter 206 with CSF may degrade the filter, for example by clogging the filter, or may allow microbes to cross the filter. The system 100 is advantageously configured such that, if the collection chamber 200 is mounted generally vertically, the float member 230 and seal plug 232 will seal off flow between the collection chamber 200 and the inflow port 212 before draining fluid reaches the filter. In one embodiment, the system will prevent drained fluid from contacting the filter if the collection chamber is mounted at an angle of 10 degrees or less from vertical in two axes at 50 centimeters of $H_2O$. In at least another embodiment, the system will seal the collection chamber at pressures less than 122 centimeters of $H_2O$, before fluid reaches the filter.

The system 100 is useful for providing controlled external drainage and monitoring of CSF from the brain or lumbar spine subarachnoid space. The system may also be used for sampling CSF, providing temporary sterile external drainage of CSF, and/or for monitoring of ICP with the connection of a pressure transducer to the stopcock 108 connected with the catheter 102. In at least one embodiment, connections between the catheter 102 and tubings 112, 114 may be made using stopcocks, and/or Luer lock connections 110, and or other connectors known in the art. The system may further include access ports or sites, for example needle free access ports known in the art.

Referring again to FIGS. 1-3, the system preferably includes support members known in the art such as pole clamps 120 or rope attachment members 132 (FIG. 8) for mounting the system to an IV pole 118 or the patients bed. The system may further include a support member 224 for retaining the drainage bag 104 to the collection chamber 200. The support member 224 may include a stopcock support 226 for a stopcock 108, and a drainage bag support 228. The collection chamber may further include at least one clip 216 for retaining the inflow line 112.

The system may be made from compatible materials known in the art such as plastics, PTFE, and silicone. In one embodiment, the device includes latex free materials. The materials forming the device should preferably be compatible with medical sterilization systems, for example ethylene oxide gas sterilization or radiation sterilization. The system may be formed by connecting together the various portions using snap fittings, adhesives, heat, screws, rivets, sonic welding or other connection techniques known in the art.

In an embodiment of a method in accordance with aspects of the invention, bodily fluid is received in a collection chamber through an inflow port disposed in the top of the container. As the chamber accumulates the received fluid, the fluid applies an upward buoyant force to a float member pivotally mounted at the top of the container with a hinge. In response to the upward buoyant force, the float member pivots upward about the hinge. At a certain volume of fluid accumulated in the chamber, the float member closes the inflow port thereby stopping flow of fluid into the chamber. The method thus includes the steps of moving the float between a closed configuration, in which fluid is prevented from flowing into the chamber, to an open configuration in which fluid may flow or drain into the collection chamber.

The method also vents the chamber as bodily fluid is received. In one aspect, the step of venting includes preventing the passage in or out of the chamber of liquid through means of an hydrophobic filter. In another aspect the venting step includes passing vented fluid past an anti-microbial agent.

In other aspects, the method includes closing the inflow port with a seal plug having a tip or apex that is continually within the inflow port during both the closed configuration and the open configuration. The mounting of the pivoting float member may be performed by a hinge having a hinge arm and hinge pins that are selected to limit torsional motion of the float member so that the float pivots in only one plane. By selecting the relative sizes of the chamber and float, the angle of movement of the float during pivoting motion can also be limited.

Figure 9:
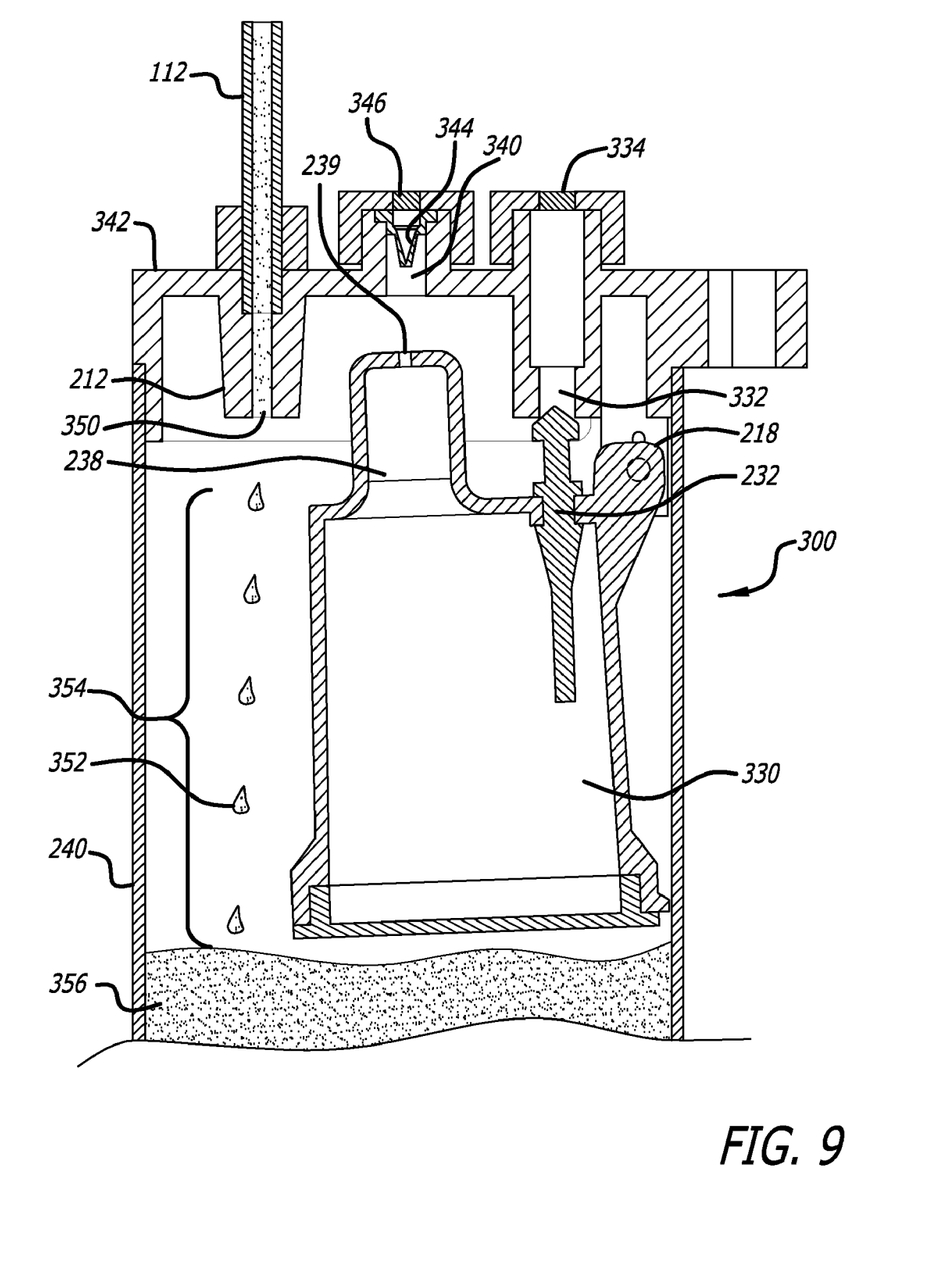
FIG. 9 provides a cross-sectional view of another embodiment in accordance with aspects of the invention in which a seal plug located on a pivoting float member is used to seal a first vent port to limit the flow of bodily fluid from a patient into the collection chamber; the embodiment also shows a second vent port having a one-way valve to provide a vent for air to flow into the chamber when the collected fluid is to be drained.

Turning now to FIG. 9, another embodiment is shown. As with the previous embodiment described above, this embodiment also limits the volume of bodily fluids drained from a patient. Rather than directly plugging the inflow port 212 to limit flow as was shown and described in the previous embodiment, this embodiment limits fluid from entering and filling the collection chamber 300 by using the seal plug 232 disposed on a pivoting float member 330 to seal a first vent port 332 of the collection chamber once the chamber has filled sufficiently. In this way, bodily fluid from the patient is allowed to flow into the collection chamber to displace air, which flows out the first vent port. As the inflow of bodily fluid proceeds to fill the collection chamber, the float member pivots or rotates in response to the bodily fluid until the seal plug 232 mounted to the float member seals the first vent. Sealing the first vent prevents the further displacement of air in the collection chamber and as a result, the pressure in the collection chamber will equal the patient fluid pressure and flow of the patient's bodily fluid into the collection chamber will cease. The first vent includes a first filter 334 that may be the same as described above in relation to the filter 206 of the first embodiment.

The process of collecting bodily fluid in this embodiment is similar to that of the previous embodiment. The outflow port (not shown) of the collection chamber is closed, in this embodiment by closing a stopcock 108 located on an outflow tube 114 from the chamber (see FIG. 1), although other means for closing the outflow port may be devised. The inflow port 212 of the chamber is opened, in this embodiment, by opening a stopcock 116 located on an inflow tube 112 between the patient and the chamber (see FIG. 1).

To drain the bodily fluid collected in the collection chamber 300, air must be allowed to enter the chamber to displace the fluid drained. Because the inflow port is closed by means of an upstream clamp or stopcock 116 in this case (see FIG. 1) and the first vent 332 is sealed by the seal plug 232 as shown in FIG. 9, fluid cannot enter the collection chamber through these two paths and drainage is severely restricted or prevented. To provide another path for air to enter the collection chamber to displace bodily fluid draining from the collection chamber, a second vent port 340 is provided in the top member 342. In this embodiment, a one-way valve (check valve) 344 with a low cracking pressure is disposed in the second vent. The one-way valve is disposed in the second vent to permit the inflow of air from the surrounding atmosphere into the collection chamber through the second vent when the cracking pressure is experienced and the one-way valve opens but will not permit the outflow of either liquid or gas from the collection chamber through the second vent. The second vent also includes a second filter 346 that functions in the same way as the filter 334 in the first vent 332 functions, and may therefore be formed of the same materials. The one-way valve referenced above may take various forms well known to those skilled in the art and consequently, no further details are provided herein.

To drain collected bodily fluid from the collection vessel 300 in the embodiment of FIG. 9, the flow inlet 212 is closed, through closing the inlet stopcock 116 (FIG. 1) in this embodiment. The flow outlet 222 is opened, through opening the drain stopcock 108 (FIG. 1) in this embodiment. It is to be noted that arrangements and devices other than the upstream and downstream stopcocks shown and described here may be devised to achieve the same effects. As gravity pulls on or applies outflow pressure on the fluid in the collection chamber 300 to tend to cause it drain out of the chamber, the air pressure in the chamber will reduce below atmospheric pressure thereby creating a pressure differential across the one-way valve 344 disposed in the second vent. When this pressure differential becomes large enough so that it equals the one-way valve's cracking pressure, the one-way valve will open to allow air from the surrounding atmosphere to flow into the collection chamber to replace the out-flowing collection chamber fluid, thereby enabling drainage of the chamber. As the collection chamber drains, the float member 330 will pivot downwards thereby opening the first vent 332 rendering the collection chamber once again ready to collect further patient bodily fluid once the upstream stopcock 116 is opened.

To stop the out-flow of fluid from the collection chamber 300 and resume collection of the patient's bodily fluid, the outflow port 222 (not shown) is closed and the inflow port 212 is opened. In this embodiment, the foregoing is effected by closing the drain stopcock 108 and opening the fluid inlet stopcock 116 (FIG. 1). It will be noted that the top member 342 of the collection chamber 300 in this embodiment has been modified from that in the first embodiment. In the present embodiment, the top member includes the same inflow port 212 as the first embodiment but at a different location, as will be discussed in more detail below. Two vent ports are provided, i.e., a first vent port 332 through which air flows out of the collection chamber and a second vent port 340 through which air may flow into the collection chamber. Both include filters 334 and 346 but the second vent port also includes a one-way valve 334 as described above.

The embodiment of FIG. 9 also illustrates a modified float design 330 that facilitates visualization of the flow of bodily fluid into the collection chamber 300 and the amount of fluid remaining. The side wall 240 in this collection chamber is also transparent and although not shown, may include various types of indicia to visually indicate to the observer the quantity of bodily fluid collected. In addition, the inflow port 212 includes a drop former 350 so that drops 352 of bodily fluid are formed as the fluid flows into the collection chamber. In accordance with a feature of this embodiment, the top member 342 and the float 330 are specifically designed in relation to each other so that the inflow port 212 and the drops of bodily fluid being collected from the patient are more clearly visible to an observer. In the embodiment shown in FIG. 9, the inflow port is located on the opposite side of the collection chamber from the hinge 218 used to mount the float member 330. Additionally, the float member has a smaller size than that of the float member 230 in FIGS. 2 through 8 so that it does not extend to a position under the inflow port. Therefore, the path 354 of the drops 352 of bodily fluid entering the collection chamber from the inflow port to accumulate and fill the chamber are not blocked from view by the float member 330 and are more easily seen by an observer.

It will be noted that the float member 330 in the embodiment of FIG. 9 includes the same chimney extension 238 with a pressure equalization hole 239 and may be filled with air or other substance contributing to the buoyancy of the float member as in the previous float member and as previously discussed. Additionally, the seal plug 232 and the hinge 218 are mounted to the float member 330 and function in the same manner as those devices in the previous float member 230.

Thus there has been shown and described a body fluid drainage system including a mechanical volumetrically controlled shut off device. The shut off device automatically shuts off flow of fluid when a desired volume of drained fluid is reached and automatically opens up again, permitting further flow, when the user drains the fluid out of the shut off device. One embodiment of the present invention provides for volume limited drainage of cerebro-spinal fluid (CSF). The system provides for volume limited CSF drainage from the brain or from the spine. Also show and described is a method for volumetrically controlled drainage of CSF using the body fluid drainage system described herein.

The invention may be embodied in other forms without departure from the spirit and essential characteristics thereof. The embodiments described therefore are to be considered in all respects as illustrative and not restrictive. Although the present invention has been described in terms of certain preferred embodiments, other embodiments that are apparent to those of ordinary skill in the art are also within the scope of the invention. Accordingly, the scope of the invention is intended to be defined only by reference to the appended claims.

We claim:

1. A bodily fluid drainage system, comprising:
    a fluid collection chamber formed by a top member connected to a bottom member by a side wall, the collection chamber comprising a first hinge component formed at a fixed position on at least one of the top member and the side wall;
    an inflow port disposed in the top member and configured for receiving bodily fluid into the collection chamber, the inflow port including a first valve component with which the inflow port may be configured to an open configuration at which fluid flows into the collection chamber through the inflow port and a closed configuration at which fluid is blocked from flowing into the collection chamber through the inflow port;
    a vent port open to atmospheric pressure disposed in the top member; and
    a buoyant float member disposed in the collection chamber below the inflow port, the buoyant float member having a hinge arm with a float member chamber disposed at a first end of the hinge arm and a second hinge component located at a second opposing end of the hinge arm, the second hinge component being pivotally connected with the first hinge component of the fluid collection chamber wherein the buoyant float member is configured to be buoyant in bodily fluid, and thereby moves pivotally according to the amount of fluid in the fluid connection chamber, the buoyant float member also having a second valve component located on the float member chamber adjacent the first end of the hinge arm, the second valve component configured to interact with the first valve component of the inflow port such that when the float member chamber moves pivotally downward, the interaction of the second valve component and first valve component place the inflow port in the open configuration, and such that when the float member chamber moves pivotally upward in response to buoyant force of bodily fluid filling the chamber, the interaction of the second valve component and first valve component place the inflow port in the closed configuration when the bodily fluid in the chamber reaches a predetermined level.

2. The bodily fluid drainage system of claim 1 wherein the second valve component comprises a seal plug mounted on the float member chamber below the inflow port and moving with the float member chamber, the seal plug being located so as to allow flow of bodily fluid through the inflow port into the collection chamber in the open configuration when the chamber has no fluid in it and closes the inflow port so as to prevent the flow of bodily fluid through the inflow port into the collection chamber in the closed configuration when a predetermined volume of bodily fluid collects in the collection chamber.

3. The bodily fluid drainage system of claim 2 wherein the seal plug has a conical shape, a diameter of which is larger than an opening of the inflow port to completely block the inflow port when in the closed configuration to prevent the flow of bodily fluid into the chamber.

4. The bodily fluid drainage system of claim 2 wherein the seal plug is elastically compliant to accommodate an accumulation of tolerances between the float member and the inflow port that could produce a misalignment between the seal plug and inflow port sufficient to prevent said seal plug from fully closing the inflow port when the bodily fluid has reached the predetermined level.

5. The bodily fluid drainage system of claim 3 wherein the conical shape of the seal plug includes an apex, the float member and seal plug disposed in the chamber so that the apex is within the inflow port when in the open configuration and also when in the closed configuration.

6. The bodily fluid drainage system of claim 1 wherein:
    the float member chamber includes a top portion at which is disposed a hollow chimney extension having a pressure equalization hole at a top surface, the pressure equalization hole configured to communicate with an interior of the float member chamber to equalize interior pressure with outside pressure;
    wherein a length of the hollow chimney extension is selected to place the equalization hole high up in the collection chamber above the collected fluid level thereby preventing the collected fluid from entering the float member lumen under normal operating conditions.

7. The bodily fluid drainage system of claim 6 further comprising a seal plug mounted on a top portion of the float member chamber below the inflow port and moving with the float member chamber, and located so as to allow flow of bodily fluid through the inflow port into the collection chamber in the open configuration when the chamber is filling and closes the inflow port so as to prevent the flow of bodily fluid through the inflow port into the collection chamber in the closed configuration when a predetermined volume of bodily fluid collects in the collection chamber;
    wherein the seal plug is positioned on the float member chamber between the chimney extension and the hinge.

8. The bodily fluid drainage system of claim 6 wherein the pressure equalization hole has a diameter that is selected to be small in size so that it inhibits the movement of the bodily fluid through the equalization hole to thereby avoid changes in buoyancy of the float member chamber.

9. The bodily fluid drainage system of claim 1 wherein the second hinge component includes:
    two hinge pins located on either side of the hinge arm, wherein the width of the hinge arm and locations of the pins are selected to provide torsional stability to the float member; and
    the first hinge component comprises two hinge pin receiving members disposed on the fluid collection chamber for receiving the two hinge pins to thereby pivotally mount the float member.

10. The bodily fluid drainage system of claim 9 further comprising a seal plug mounted on a top portion of the float member chamber below the inflow port and moving with the float member chamber, and located so as to allow flow of bodily fluid through the inflow port into the collection chamber in the open configuration when the chamber is filling and closes the inflow port so as to prevent the flow of bodily fluid through the inflow port into the collection chamber in the closed configuration when a predetermined volume of bodily fluid collects in the collection chamber;

wherein the seal plug is positioned on the float member chamber adjacent the hinge.

11. The bodily fluid drainage system of claim 1 wherein the float member is configured so that its pivotal movement is limited to a predetermined angle.

12. The bodily fluid drainage system of claim 11 wherein:
the side wall has an inner surface having an inner diameter; and
the float member chamber has a bottom portion having an outer diameter that is smaller than the inner diameter of the side wall by a predetermined distance such that pivotal movement of the hinged float member chamber in the direction of the open configuration is limited to the predetermined angle by contact of the bottom portion of the float member chamber with the inner surface of the side wall.

13. The bodily fluid drainage system of claim 1 further comprising a filter connected with the vent port wherein the filter is configured to be hydrophobic.

14. The bodily fluid drainage system of claim 1 further comprising a filter connected with the vent port wherein the filter is configured to be antimicrobial.

15. The bodily fluid drainage system of claim 1 wherein the side wall of the fluid collection chamber is transparent so that contents of the collection chamber can be seen directly through the side wall.

16. The bodily fluid drainage system of claim 15 wherein the side wall of the fluid collection chamber includes volume markings.

17. A volume-limited cerebrospinal fluid (CSF) drainage system, comprising:
a CSF collection chamber formed by a top member connected to a bottom member by a side wall, the collection chamber comprising a first hinge component formed at a fixed position on at least one of the top member and the side wall;
an inflow port disposed in the top member and configured for receiving CSF into the collection chamber, the inflow port including a first valve component with which the inflow port may be configured to an open configuration at which fluid flows into the collection chamber through the inflow port and a closed configuration at which fluid is blocked from flowing into the collection chamber through the inflow port;
a vent port open to atmospheric pressure disposed in the top member;
a buoyant float member having a float member chamber configured to be buoyant in CSF fluid, the float member chamber having a top portion and a bottom portion disposed in the collection chamber below the inflow port, the float member top portion being pivotably connected with the first hinge component of the chamber by a second hinge component such that the float member chamber moves pivotally downward when there is no CSF in the collection chamber and moves pivotally upward in response to buoyant force of CSF flowing into the collection chamber; and
a seal plug mounted on the top portion of the float member chamber adjacent the second hinge component and below the inflow port so as to interact with the first valve component in accordance with pivotal movement of the float member chamber, and moving with the float member chamber downward thereby placing the inflow port in the open configuration so as to allow flow of CSF through the inflow port into the collection chamber and moving with the float member chamber upward thereby placing the inflow port in the closed configuration so as to prevent the flow of CSF through the inflow port into the collection chamber when a predetermined volume of CSF collects in the collection chamber;
wherein the seal plug has a conical shape, a diameter of which is larger than an opening of the inflow port to completely block the inflow port when in the closed configuration to prevent the flow of CSF into the collection chamber;
the top portion of the float member chamber includes a hollow chimney extension having a pressure equalization hole at a top surface, the pressure equalization hole configured to communicate with an interior of the float member chamber to equalize interior pressure with outside pressure;
wherein a length of the hollow chimney extension is selected to place the equalization hole high up in the collection chamber above the collected CSF level thereby preventing the collected CSF from entering the float member lumen under normal operating conditions;
wherein the pressure equalization hole has a diameter that is selected to be small in size so that it inhibits the movement of CSF through the equalization hole to thereby avoid changes in buoyancy of the float member chamber;
wherein the seal plug is positioned on the float member chamber between the chimney extension and the second hinge component;
wherein the wall of the fluid collection chamber is transparent so that contents of the collection chamber can be seen directly through the wall.

18. A bodily fluid drainage system, comprising:
a fluid collection chamber formed by a top member connected to a bottom member by a side wall, the collection chamber comprising a first hinge component formed in a fixed position on at least one of the top member and the side wall;
an inflow port disposed in the top member and configured for receiving bodily fluid into the collection chamber;
a first vent port open to atmospheric pressure disposed in the top member, the first vent port including a first valve component with which the first vent port may be configured to an open configuration at which air flows out of the collection chamber through the first vent port and a closed configuration at which air is blocked from flowing out of the collection chamber through the first vent port; and
a buoyant float member disposed in the collection chamber below the first vent port, the buoyant float member having a hinge arm with a float member chamber disposed at a first end of the hinge arm and a second hinge component located at a second opposing end of the hinge arm, the second hinge component being pivotally connected with the first hinge component of the fluid collection chamber wherein the buoyant float member is configured to be buoyant in bodily fluid, and thereby moves pivotally according to the amount of fluid in the fluid connection chamber, the buoyant float member also having a second valve component located on the float member chamber adjacent the first end of the hinge arm, the second valve component configured to interact with the first valve component of the vent port such that when the float member chamber moves pivotally downward, the interaction of the second valve component and first valve component places the first vent port in the open configuration, and such that when the float member moves pivotally upward in response to buoyant force of bodily fluid flowing into the chamber, the interaction of the second valve component and first valve component place the first vent port in the closed configuration when the bodily fluid in the chamber reaches a predetermined level.

19. The bodily fluid drainage system of claim 18 further comprising a second vent port disposed in the top member configured to permit air to flow into the collection chamber.

20. The bodily fluid drainage system of claim 19 further comprising a one-way valve having a cracking pressure mounted in the second vent port to permit air to flow into the collection chamber through the second vent port when the cracking pressure has been met but to prevent air from flowing out of the chamber through the second vent port when the cracking pressure has not been met; and wherein the buoyant float member is further configured to move pivotally downward in an open configuration leaving the first vent port open and to move pivotally upward in a closed configuration in response to buoyant force of bodily fluid filling the chamber closing the first vent port when the bodily fluid in the chamber reaches a predetermined level.

21. The bodily fluid drainage system of claim 20 further comprising an outlet port located at the bottom member through which fluid may flow out of the collection chamber;

wherein the cracking pressure of the one-way valve is selected to be approximately equal to a pressure differential created within the collection chamber by fluid flowing out through the outlet port.

22. The bodily fluid drainage system of claim 20 wherein the inlet port is located in the top member at a position opposite the position of the first hinge component and wherein the collection chamber has an inner diameter and the buoyant float member chamber has an outer diameter that is selected to be smaller than the inner diameter of the collection chamber such that the buoyant member chamber is not located under the inlet port in either the open or closed configurations of the first vent port.

23. The bodily fluid drainage system of claim 22 wherein the side wall of the fluid collection chamber is transparent so that the flow of bodily fluid into the collection chamber through the inflow port can be seen directly through the side wall.

24. The bodily fluid drainage system of claim 20 further comprising a seal plug mounted on the float member chamber below the first vent port and moving with the float member chamber, the seal plug being located so as to allow air to flow out of the first vent port from the collection chamber in the open configuration when the chamber has no fluid in it and closes the first vent port so as to prevent the flow of air out of the collection chamber in the closed configuration when a predetermined volume of bodily fluid collects in the collection chamber.

25. The bodily fluid drainage system of claim 24 wherein the seal plug has a conical shape, a diameter of which is larger than an opening of the first vent port to completely block the first vent port when in the closed configuration to prevent the flow of air out of the chamber.

26. The bodily fluid drainage system of claim 25 wherein the conical shape of the seal plug includes an apex, the float member and seal plug disposed in the chamber so that the apex is within the first vent port when in the open configuration and also when in the closed configuration.

27. The bodily fluid drainage system of claim 20 wherein:
the float member includes a top portion at which is disposed a hollow chimney extension having a pressure equalization hole at a top surface, the pressure equalization hole configured to communicate with an interior of the float member to equalize interior pressure with outside pressure;
wherein a length of the hollow chimney extension is selected to place the equalization hole high up in the collection chamber above the collected fluid level thereby preventing the collected fluid from entering the float member lumen under normal operating conditions.

28. The bodily fluid drainage system of claim 20 wherein the hinge includes:
a hinge arm having a width disposed on the float member;
two hinge pins located on either side of the hinge arm, wherein the width of the hinge arm and locations of the pins are selected to provide torsional stability to the float member; and
two hinge pin receiving members disposed on the collection chamber for receiving the two hinge pins to thereby pivotally mount the float member.

29. The bodily fluid drainage system of claim 28 wherein the float member is configured so that its pivotal movement is limited to a predetermined angle.

30. The bodily fluid drainage system of claim 29 wherein:
the side wall has an inner surface having an inner diameter; and
the float member chamber has a bottom portion having an outer diameter that is smaller than the inner diameter of the side wall by a predetermined distance such that pivotal movement of the hinged float member in the direction of the open configuration is limited to the predetermined angle by contact of the bottom portion of the float member chamber with the inner surface of the side wall.

\* \* \* \* \*